United States Patent
Abrams

(10) Patent No.: US 7,048,477 B2
(45) Date of Patent: May 23, 2006

(54) DRILL MEASUREMENT STOPS

(75) Inventor: Steven Abrams, Flanders, NJ (US)

(73) Assignee: I.D.M.S., L.L.C., Budd Lake, NJ (US)

( * ) Notice: Subject to any disclaimer, the term of this patent is extended or adjusted under 35 U.S.C. 154(b) by 0 days.

(21) Appl. No.: 10/878,928

(22) Filed: Jun. 28, 2004

(65) Prior Publication Data

US 2004/0265082 A1    Dec. 30, 2004

Related U.S. Application Data

(60) Provisional application No. 60/483,787, filed on Jun. 30, 2003.

(51) Int. Cl.
B23B 51/00 (2006.01)
B23B 51/02 (2006.01)

(52) U.S. Cl. .................. 408/1 R; 408/16; 408/202; 408/226; 408/239 A; 408/241 S; 433/75; 433/165

(58) Field of Classification Search ............. 408/1 R, 408/14, 16, 57, 59, 202, 26, 238, 239 A, 408/239 R, 241 S, 226; 433/72, 75, 134, 433/165, 166, 102
See application file for complete search history.

(56) References Cited

U.S. PATENT DOCUMENTS

| 3,358,826 | A | * | 12/1967 | Siegel ............... 206/368 |
| 3,961,422 | A | * | 6/1976 | Riitano et al. .......... 433/75 |
| 4,205,444 | A | * | 6/1980 | Weissman ............ 433/165 |
| 4,255,145 | A | * | 3/1981 | Weissman ............ 433/165 |
| 4,526,542 | A | * | 7/1985 | Kochis ............... 433/165 |
| 4,710,075 | A | * | 12/1987 | Davison ............. 408/202 |
| 4,904,130 | A | * | 2/1990 | Gorman ............... 408/16 |
| 4,993,894 | A | * | 2/1991 | Fischer et al. ......... 408/14 |
| 5,098,293 | A | * | 3/1992 | Loof et al. ........... 433/165 |
| 5,102,271 | A | * | 4/1992 | Hemmings ........... 408/226 |
| 5,147,164 | A | * | 9/1992 | Fraver ............... 408/202 |
| 5,197,833 | A | * | 3/1993 | Mayer et al. ......... 408/226 |
| 5,366,374 | A | * | 11/1994 | Vlassis ............... 433/165 |
| 5,393,178 | A | * | 2/1995 | Daraz ................ 409/234 |
| 5,587,284 | A | * | 12/1996 | Brattesani ............ 433/72 |
| 5,735,690 | A | * | 4/1998 | Malentacca ........... 433/102 |
| 5,890,897 | A | * | 4/1999 | Kruger et al. .......... 433/75 |
| 6,062,859 | A | * | 5/2000 | Filhol ................ 433/165 |
| 6,199,821 | B1 | * | 3/2001 | Job ................... 248/682 |
| 6,379,155 | B1 | * | 4/2002 | Riitano et al. ......... 433/224 |
| 6,514,258 | B1 | * | 2/2003 | Brown et al. .......... 606/80 |

(Continued)

FOREIGN PATENT DOCUMENTS

FR    2613212 A1 * 10/1988

Primary Examiner—Boyer D. Ashley
Assistant Examiner—Michael W. Talbot
(74) Attorney, Agent, or Firm—Benjamin Appelbaum

(57) ABSTRACT

A depth stop for use with a drill bit comprises a tubular body having an opening therethrough. Used with a drill bit whose bit portion includes a cutting end, and a shank portion, the depth stop is frictionally positionable on the bit portion at a specified point from the cutting end, thereby indicating a specified depth. Depth stops are manufactured in different colors, each color corresponding to a specified range of drill bits that the depth stops will fit. The depth stops, manufactured from a sterilizable material, are intended for single use. The depth stop can be used with a drill bit and drill extender, where one or more depth stops provide multiple visual points of reference for the operator. The depth stops can be quickly mounted onto most any manufacturer's drill bits.

11 Claims, 3 Drawing Sheets

U.S. PATENT DOCUMENTS

| | | |
|---|---|---|
| 6,575,747 B1* | 6/2003 | Riitano et al. ............... 433/102 |
| 6,739,872 B1* | 5/2004 | Turri ........................... 433/75 |
| 2002/0094508 A1* | 7/2002 | Lorenzi ....................... 433/165 |
| 2002/0172923 A1* | 11/2002 | Strong et al. ................ 433/165 |
| 2003/0049586 A1* | 3/2003 | Kumar ........................ 433/165 |
| 2003/0096213 A1* | 5/2003 | Hickok et al. ............... 433/119 |
| 2004/0129125 A1* | 7/2004 | Colquhoun ................... 83/835 |
| 2004/0241608 A1* | 12/2004 | Hickok ........................ 433/119 |

* cited by examiner

US 7,048,477 B2

DRILL MEASUREMENT STOPS

CROSS-REFERENCE TO RELATED APPLICATION

This application claims the benefit of U.S. Provisional Patent Application Ser. No. 60/483,787, filed 30 Jun. 2003, the contents of which are hereby incorporated by reference.

FIELD OF THE INVENTION

The present invention is a device for use in dental and medical procedures involving drilling. A particular embodiment is a depth measurement stop which is attached onto a drill bit, indicating to the drill operator that the drill has reached a specified depth.

BACKGROUND OF THE INVENTION

In the field of performing dental osteotomies for the placement of an implant to replace a tooth, it is necessary to prepare the site to receive the implant therein. This is generally done by means of a handpiece and drill bit, drilling into the existing bone to both a specified depth and a specified diameter before inserting the implant into the site.

Some of the drill bits currently used for this procedure contain markings thereon to indicate the depth of the bit. These markings, however, are generally a band of a dark color, notches engraved onto the bit, or alternating color bands to represent a range of depths. In the mix of water, saliva and sometimes blood present in the mouth, the location of the implant site itself (often in or towards the rear of the mouth), and the generally high speed of rotation of the drill bit (several hundred or more revolutions per minute), even under the best of circumstances it is difficult for the operator to know precisely when a given depth has been reached. It is often necessary to stop drilling, and actually measure the depth using a probe of known depths, and then continue drilling if the necessary depth has not been reached, until the desired depth has been reached. Although it is feasible to perform this cycle of stopping, measuring, restarting etc., during an implant procedure, doing this several times often adds to the stress of the patient and/or the operator, and this cycling is neither as convenient nor as useful as being able to know when a specific depth has been reached, and to stop at that point.

While a number of different types of drill stops have been described in the prior art, there is still a long-felt and unmet need for a depth measurement stop which can be quickly mounted onto most any manufacturer's drill bits, can be provided in a variety of diameters for use on various sized drill bits, can be readily sterilized by autoclaving, can be color coded for ease of identification during use, and are intended for a single use. Embodiments of the present invention, described in further detail in the following sections, meet these needs.

BRIEF SUMMARY OF THE INVENTION

It is an object of the present invention is to provide a device that will provide a means to indicate the depth of a drill bit while drilling into a surface.

Still another object of the present invention is to provide a device that can be produced in a variety of diameters for use on different sized drill bits.

Another object of the present invention is to provide a device that can be used on a variety of different drill systems which correspond to a variety of different implants.

Yet another object of the present invention is to provide a device that can be color coded for ease of identification during use.

Another object of the present invention is to provide a device that is economical to manufacture, can be sterilized, and which is intended for single use.

An embodiment of the present invention comprises the combination of a drill bit with a depth stop that is positioned on the bit at a specified depth. When the bit reaches the specific depth, it becomes obvious to the operator that that specified depth has been reached, and the operator can be assured that the depth is accurate. The depth stop has a tubular body, like an O-ring, that is mounted on the shaft of the drill bit, towards the cutting end of the drill bit. The depth stop is positioned such that the operator can still maintain the tactile feel necessary to know how the drilling is proceeding. Other embodiments of the present invention include the combination of a drill bit with a drill bit extender, and the use of at least one depth stop mounted on the drill bit, and a second depth stop mounted on the drill bit extender. Using the combination of multiple depth stops on the drill bit and drill bit extender, the operator is provided with more than one visual point of reference. The depth stops are manufactured in different colors, each color corresponding to a specified range of drill bits that the depth stops will fit. The depth stop are manufactured from a sterilizable material, and intended for single use. The depth stop can be used with a drill bit and drill extender, where one or more depth stops provide multiple visual points of reference for the operator. The depth stops can be quickly mounted onto most any manufacturer's drill bits.

DETAILED DESCRIPTION OF THE INVENTION

Figure 1:
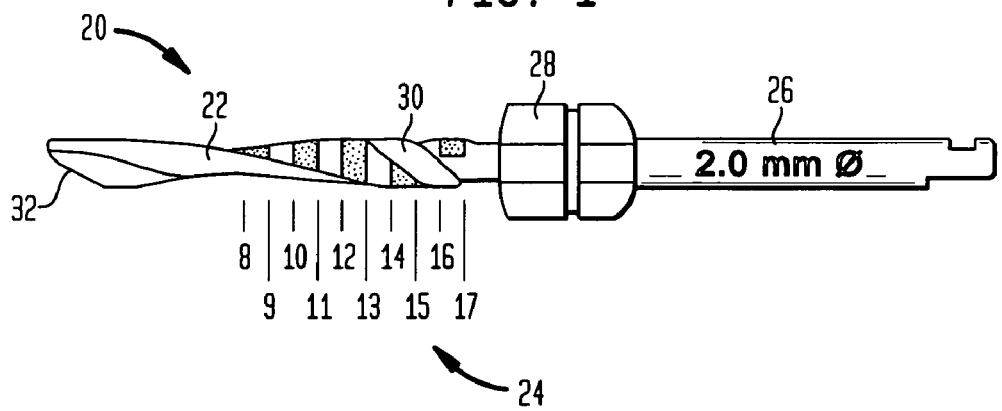
FIG. 1 is a perspective view of a representative drill bit. The diameter of the bit is engraved on the shank, and the alternating light and dark markings on the bit indicate depth, in millimeters.
Figure 2:
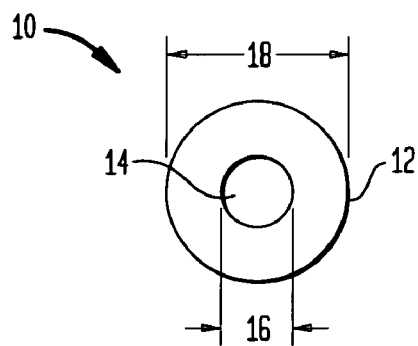
FIG. 2 is a plan view of a depth stop of the present invention.
Figure 3:
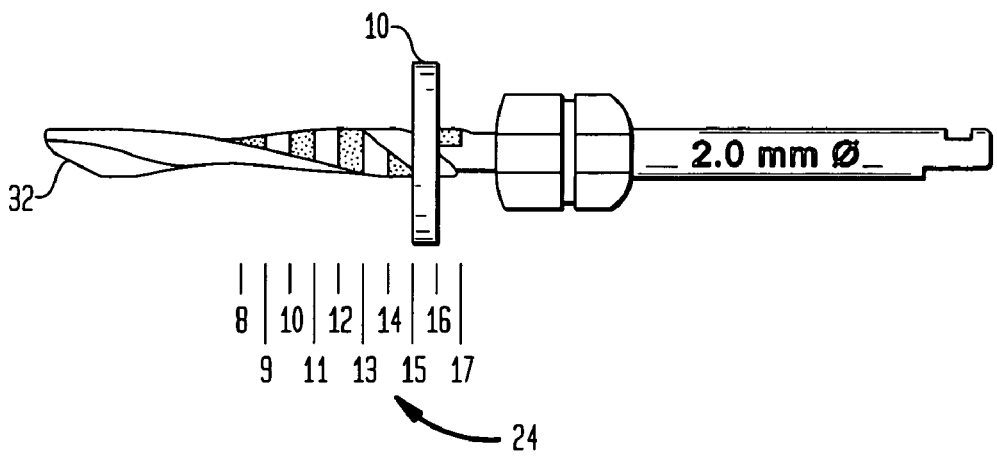
FIG. 3 illustrates a depth stop of the present invention attached to the drill bit of FIG. 1.

The present invention comprises a system of implant drill measurement stops 10 (also referred to herein as drill stops or depth stops) for attachment onto a drill bit 20 (FIG. 1). The drill stops decisively mark the depth measurement of the implant drill. An embodiment of the present invention is a drill stop 10 that has a body 12 with an opening 14 therein, an inner diameter 16 and outer diameter 18 (FIG. 2), the inner diameter being sized such that when the drill stop 10 is mounted on a drill bit, it provides a snug fit thereon. This facilitates the visualization of the depth of the osteotomy site while the drill is in operation in the field to reach the desired depth as marked with the stop 10. An embodiment of the present invention employs drill stops 10 that are color coded to indicate the range of drill bit diameters on which a particular drill stop can be used, enabling the user (also referred to herein as either operator or practitioner) to determine rapidly which stop can be associated with a particular diameter bit (Table 1).

FIG. 1 illustrates a typical drill bit used for preparing a dental site to receive an implant. Drill bit 20 comprises a bit (or bit portion) 22 with a plurality of depth indicia 24, a nub 28, and a shank 26 which is received within a handpiece 80 (not shown in FIG. 1, but see FIG. 5). One or more grooves 30 (which may also be referred to herein as channel or flute) is formed within the bit portion 22 and, as known to those skilled in the art, facilitates debris removal from the site.

The nub 28 of the drill bit embodiment shown in FIG. 1, formed as an integral part of the drill, is not movable. This type of drill bit is intended for use with external irrigation sources, but as will be described below, an embodiment of the present invention is also suitable for drill bits including a cannula or other channel used for providing internal irrigation to the site. Other drill bit embodiments (not shown) include drill bits which lack nub 28 are also considered to be within the scope of the present invention.

The depth stop 10 is mounted on the drill bit 22 by inserting the bit through the opening 14 of the drill stop 10, and positioning the drill stop at a specified distance from the cutting end 32 of the drill bit. The drill stop 10 is frictionally mounted on the drill bit, the fit being sufficiently tight to retain the drill stop in place during the high speed rotation of the drill bit during the drilling procedure, yet with a sufficient resiliency to allow some movement of the drill stop 10 upon contact with a surface, if desired. This inventor believes this kind of resiliency cannot be obtained with prior art depth stops attached to drill bits using set screws or similar engagement mechanisms that either engage the shaft or the groove of the bit. During a procedure, the operator should be able to feel the quality of the site during the drilling phase, in order to determine the hardness or the type of bone which will receive the implant, as this can affect whether the implant will be successfully retained, or fail.

The depth stop can be mounted on a drill bit prior to sterilization, and the combination sterilized as a unit prior to use, or a sterile drill stop can be aseptically positioned on a sterile drill bit, whichever may be most convenient to a practitioner.

Embodiments of the present invention offer the practitioner the ability both to retain the tactile feel of the drill, and to visualize the progress of the drilling, and to determine when the appropriate depth has been reached based both on the feel of the drill bit 12 and the position of the drill implant stop 10. While such a "tactile feel" is difficult to describe with certainty, those skilled in the art are aware of, and will appreciate, that by paying attention to both the sounds generated by a drill bit during these procedures, as well as the feel of the device, an experienced practitioner can sense how the procedure is going, in addition to reliance on visual criteria.

The drill bit shown in the Figures is a solid bit, meant for use with an external irrigation source, but other embodiments of drill bits, such as those including a cannula therein for internally furnishing irrigating and/or cooling agents to the site, can be employed similarly and are intended to be included within the scope of the present invention.

In another embodiment (FIG. 4) a drill extender 40 is used with a drill bit 20 to increase the operating length. The drill extender shown in this Figure is intended for use with "latch type implant drills", but other types of extenders could be joined to an appropriate drill bit at the shank 26 of drill bit by means (not shown) such as either threaded or frictional engagement therewith.

Figure 6:
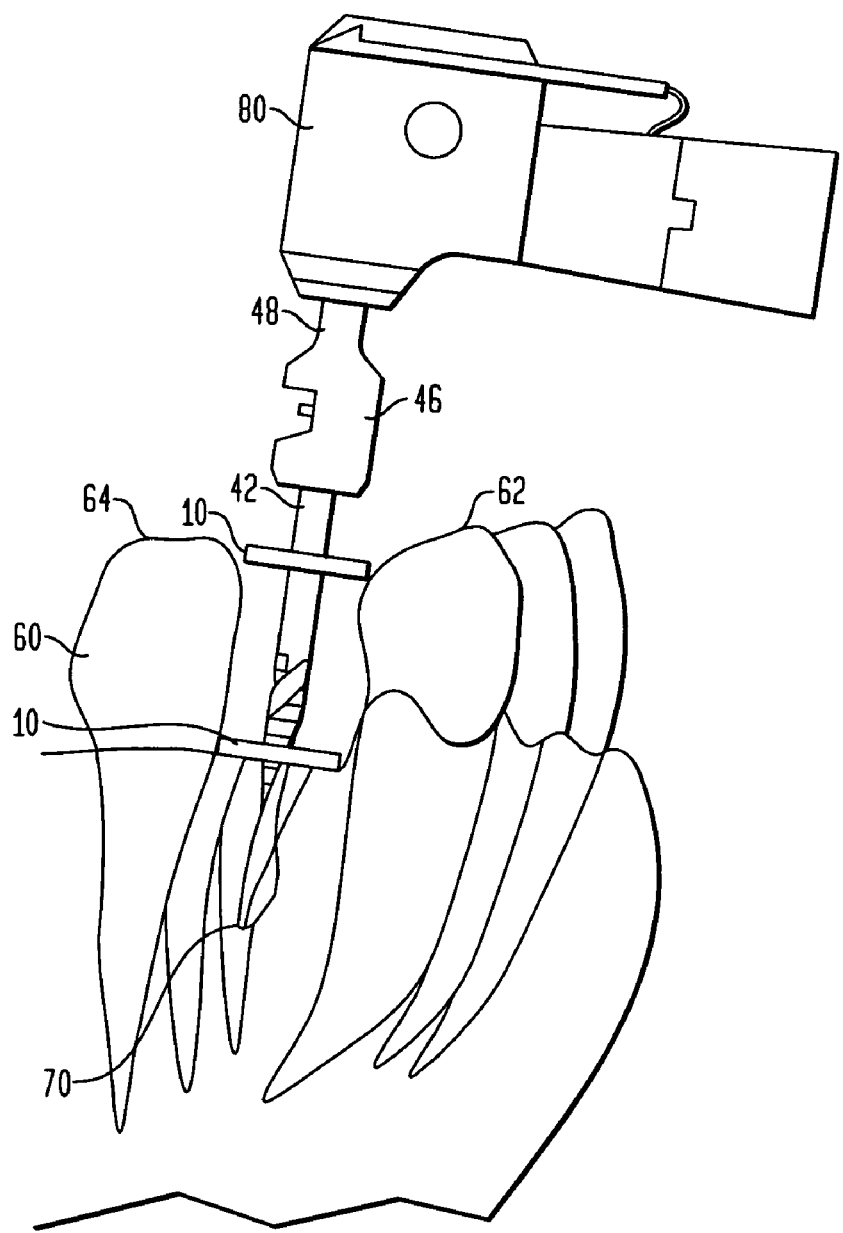
FIG. 6 is a schematic illustration of the embodiment of FIG. 4 in use during an osteotomy.

Drill extender 40 comprises a tubular shaft 42 which terminates at first end 44 and connector 46, which serves as a receptacle for the shank 26 of the drill bit 20. Drill extender 40 further includes a shank (or body) 48 terminating at second end 50 which includes neck 52 and prong 54, with prong 54, neck 52 and a portion of extender shank 48 being received within a handpiece 80 (FIG. 6). The connector 46 includes a receptacle that is similar to the handpiece's receptacle for prong 54 and neck 52.

Figure 4:
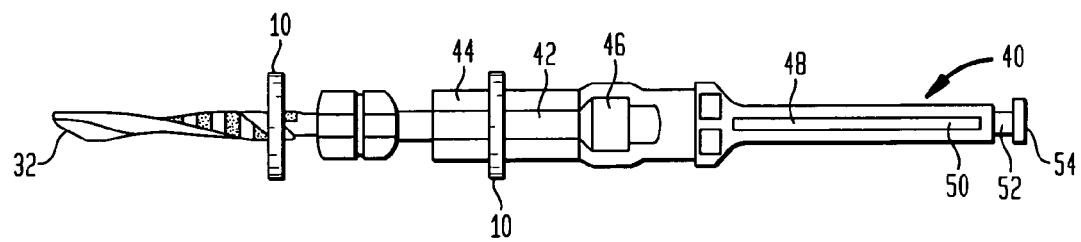
FIG. 4 illustrates a drill bit in combination with a drill extender in another embodiment of the present invention.

When a drill extender is used, it can be advantageous to employ one or more depth stops (FIGS. 4, 6). A first stop 10 is placed on the drill bit as previously described, to reference the depth of the osteotomy site, and a second stop 10 placed on the tubular shaft 42. The second stop can be used to reference the surface of a tooth adjacent to the site being prepared, such as an incisal edge ("IE"), IE1 62 or IE2 64 of a tooth 60 adjacent the osteotomy site 70 (FIG. 6). This combination enables the operator to precisely determine the depth without having to rely solely on the surgical field as the only means to visualize the depth of the drill.

Figure 5A:
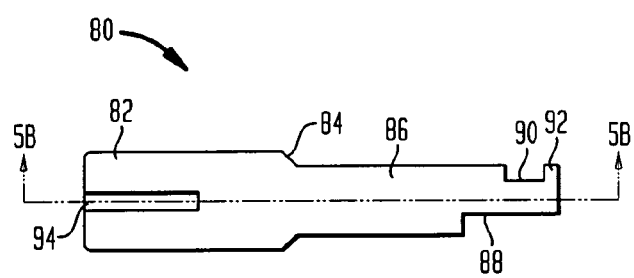
FIG. 5A illustrates another embodiment of a drill extender.
Figure 5B:
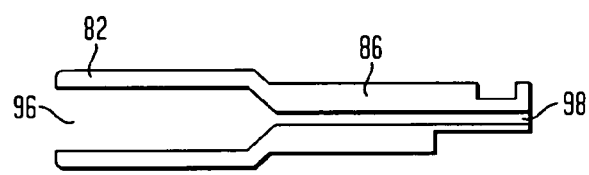
FIG. 5B is a sectional view taken along line 5B—5B of FIG. 5A.
Figure 5C:
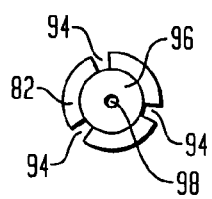
FIG. 5C is a top view of the embodiment shown in FIG. 5A.

Another drill extender embodiment is shown in FIGS. 5A–5C, in which extender 80 comprises a tubular shaft 82 which terminates at a tapered shoulder 84, which joins shank 86. Shank 86 extends as shown (FIG. 5A), having a flat neck 88, a narrow connector region 90 and which terminates at arcuate end 92, such that when inserted into a handpiece, end 92, connector region 90 and a portion of extender shank 86 are received within the handpiece 80. Tubular 82 includes several slits 94 therein. The embodiment shown in FIG. 5A includes three slits equidistantly on the perimeter of the shaft (FIG. 5C). Tubular 82 includes a channel 96 therein, the channel 96 being substantially the length of the shaft, but the length of the channel can vary with manufacturers. In the embodiment of FIG. 5C, channel 96 is wider at the end inside tubular 82 and narrower inside the shank region 86, the narrow region being designated as bore 98.

For applications outside the dental area, another surface within proximity to the site, such as a bone, ligament or other reference point can be used to provide the second reference point, and thereby determine the location for positioning of a second depth stop on the extender.

The depth stops 10 are manufactured from medical grade silicone or other materials, such as various types of natural or synthetic rubbers, EDPM rubber (ethylene-propylene-diene monomer rubber), styrene-butadiene, or BUNA-N rubber; nylon or polytetrafluoroethylene ("PTFE", sold commercially under the brand name TEFLON®, E.I. DuPont & Co., Wilmington Del.) could be used. The depth stops 10 are capable of being sterilized by autoclaving prior to use. The depth stops are intended for single use.

The depth stops can be color coded, such that the needed diameter can be accurately and quickly gauged by the operator. Thus, while the colors and associated drill bit diameters are summarized below, this list is intended to be exemplary and not limiting, as other color schemes may be utilized, and are intended to be included within the scope of the present invention:

TABLE 1

Color coding of depth stops.

| COLOR | Drill Diameter |
|---|---|
| White | 0.5–2 mm |
| Yellow | 2 mm–2.9 mm |
| Orange | 3 mm–3.9 mm |
| Blue | 4 mm–4.9 mm |
| Green | 5 mm–5.9 mm |
| Black | 6 mm–6.9 mm |

Table 1 lists the drill diameters in metric units (millimeters); it is to be understood that drill stops in sizes to accommodate dimensions in inches or fractions thereof are expressly considered as being within the scope of the present invention.

Embodiments of the present invention, initially designed to be applicable for drilling in bone for the insertion of dental implants, can be equally applicable to other procedures. Among these procedures include drilling for insertion of surgical screws, posts or other fasteners or prostheses, as is commonly performed in orthopedics, preparation of hip, knee and other joint and/or bone prostheses, neurosurgical procedures, endodontic, prostodontic and periodontic procedures, and the like. Such procedures can also include procedures performed on mammals other than humans, such as domestic pets like cats, dogs and the like, or other animals kept on farms, zoos, animal preserves and the like, and may literally cover the range from A to Z, and in between.

In the dental area, a drill bit is positioned and used within a dental handpiece 80 (see FIG. 6). Personnel in other fields may employ hand drills, or various types of electric drills, whether commercially available or supplied by various medical, dental or surgical supply houses. The present invention is intended to be applicable to other such techniques, and not limited to the field of dentistry.

Therefore, although this invention has been described with a certain degree of particularity, it is to be understood that the present disclosure has been made only by way of illustration and that numerous changes in the details of construction and arrangement of parts may be resorted to without departing from the spirit and scope of the invention.

What is claimed is:

1. A dental osteotomy device comprising:
   a drill bit, the drill bit comprising a bit portion and a shank portion, the bit portion having a cutting end and a length;
   a drill extender comprising:
   a tubular shaft;
   a connector at an end of the tubular shaft, the connector being sized to receive the drill bit shank; and
   an extender shank joined to the connector, the extender shank sized to be received within a drill;
   a plurality of depth stops,
   each depth stop comprising
   a tubular body having an opening therethrough, the opening defining an inner diameter, the inner diameter being sized to receive the drill bit or the drill extender therein;
   wherein a plurality of depth stops includes a first depth stop frictionally positioned on the bit portion at a specified distance on the length from the cutting end, the first depth stop thereby indicating a first visual reference point, the reference point being a specific depth, and wherein a second depth stop is frictionally positioned on the tubular shaft, the second depth stop thereby providing a second reference point, the second reference point being an object having a known distance and being proximate the osteotomy site.

2. The device as described in claim 1, wherein the depth stop is color coded to indicate the size range of drill bits or drill extenders onto which the depth stop can be frictionally positioned.

3. The device as described in claim 2, wherein the depth stop body is manufactured from a material that is sterilizable.

4. The device as described in claim 3, wherein the drill bit further comprises an irrigation channel extending therethrough to provide irrigation to the osteotomy.

5. The device as described in claim 4, wherein the drill is a dental handpiece.

6. An osteotomy device comprising:
   a drill bit, the drill bit comprising a bit portion and a shank portion, the bit portion having a cutting end and a length;
   a drill extender comprising:
   a tubular shaft;
   a connector at an end of the tubular shaft, the connector being sized to receive the drill bit shank; and
   an extender shank joined to the connector, the extender shank sized to be received within a drill;
   wherein a plurality of depth stops includes a first depth stop
   a plurality of depth stops, each depth stop, comprising
   a tubular body having an opening therethrough, the opening defining an inner diameter, the inner diameter being sized to receive the drill bit or drill extender therein;
   frictionally positioned on the bit portion at a specified distance on the length from the cutting end, the first depth stop thereby indicating a first visual reference point, the reference point being a specific depth, and wherein a second depth stop is frictionally positioned on the tubular shaft, the second depth stop thereby providing a second reference point, the second reference point being an object having a known distance and being proximate the osteotomy site.

7. The device as described in claim 6, wherein the depth stop is color coded to indicate the size range of drill bits or drill extenders onto which the depth stop can be frictionally positioned.

8. The device as described in claim 7, wherein the depth stop body is manufactured from a material that is sterilizable.

9. A method for controlling depth during a drilling procedure, the method comprising the steps of:
   providing a drill bit, the drill bit comprising a bit portion and a shank portion, the bit portion having a cutting end and a length;
   providing a drill extender comprising;
   a tubular shaft;
   a connector at an end of the tabular shaft, the connector being sized to receive the drill bit shank; and
   an extender shank joined to the connector, the extender shank sized to be received within a drill;
   providing a plurality of depth stops, each depth stop comprising:
   a tubular body having an opening therethrough, the opening defining an inner diameter, the inner diameter being sized to receive the drill bit or drill extender therein; and positioning a first depth stop on the bit portion at a specified distance on the length from the cutting end, the first depth stop thereby indicating a first visual reference point, the reference point being a specific depth, and wherein a second depth stop is frictionally positioned on the tubular shaft, the second depth stop thereby providing a second reference point, the second reference point being an object having a known distance and being proximate the drilling site.

10. The method for controlling depth as described in claim 9, wherein the depth stop is color coded to indicate the size range of drill bits or drill extenders onto which the depth stop can be frictionally positioned.

11. The method for controlling depth as described in claim 10, wherein the depth stop body is manufactured from a material that is sterilizable.

* * * * *